United States Patent [19]
Igarashi et al.

[11] Patent Number: 5,360,909
[45] Date of Patent: Nov. 1, 1994

[54] PHENOXYACETIC ACID COMPOUNDS AND MEDICAL PREPARATIONS CONTAINING THEM

[75] Inventors: Azuma Igarashi, Hadano; Sachiko Maeda, Nakai; Katuyoshi Sugizaki, Isehara; Takashi Shizawa, Ninomiya; Atsumi Tajima, Zama; Kenichi Abe; Shinji Ozawa, both of Hadano, all of Japan

[73] Assignee: Terumo Kabushiki Kaisha, Tokyo, Japan

[21] Appl. No.: 35,178

[22] Filed: Mar. 22, 1993

[30] Foreign Application Priority Data

Mar. 23, 1992 [JP] Japan .................. 4-064773
Jul. 24, 1992 [JP] Japan .................. 4-198541

[51] Int. Cl.$^5$ .................. C07D 471/04; C07D 471.02; A61K 31/47
[52] U.S. Cl. .................. 546/172; 560/12; 560/13; 560/17; 562/426; 562/430
[58] Field of Search .............. 514/311, 479, 567, 562; 546/172; 560/17, 12, 13; 562/426, 430

[56] References Cited

U.S. PATENT DOCUMENTS

| | | | |
|---|---|---|---|
| 4,866,196 | 9/1989 | Iwakuma | 560/12 |
| 4,948,810 | 8/1990 | Iwakuma | 514/539 |
| 5,179,105 | 1/1993 | Igarashi et al. | 514/311 |

FOREIGN PATENT DOCUMENTS

| | | |
|---|---|---|
| 0239907 | 10/1987 | European Pat. Off. |
| 0255728 | 2/1988 | European Pat. Off. |
| 0325245 | 7/1989 | European Pat. Off. |
| 0399291 | 11/1990 | European Pat. Off. |
| 3927369 | 2/1991 | Germany |
| 3927931 | 2/1991 | Germany |
| 3-258759 | 11/1991 | Japan |
| WO88/06886 | 3/1987 | WIPO |

Primary Examiner—C. Warren Ivy
Assistant Examiner—D. Margaret M. Mach
Attorney, Agent, or Firm—Burns, Doane, Swecker & Mathis

[57] ABSTRACT

Disclosed are phenoxyacetic acid compounds of formula (I):

where
X is a hydrogen atom, a lower alkyl group or a halogen atom;
R1 is a carboxyl group or a lower alkoxycarbonyl group;
Y is an oxygen atom, $$-NH\!\!\diagdown\!\!\!\!\diagup\!\!=\!S \quad \text{or} \quad -\!\!\underset{\underset{H}{|}}{N}\!-\!\!\underset{\underset{O}{\|}}{C}\!-;$$
$$-NH\diagup$$

n is an integer of from 0 to 5;
Z is

R2 is a hydrogen atom or a lower alkyl group; and
m is 0 or 1.

The compounds and their physiologically acceptable salts are used as thromboxane A2 antagonistic agents, leukotriene antagonistic agents and/or anti-allergic agents.

18 Claims, No Drawings

PHENOXYACETIC ACID COMPOUNDS AND MEDICAL PREPARATIONS CONTAINING THEM

BACKGROUND OF THE INVENTION

1. Field of the Invention

The present invention relates to novel phenoxyacetic acid compounds and medical preparations containing them.

2. Description of Prior Art

It has been suggested that thromboxane A2 and leukotrienes are closely related to serious ischemic diseases such as cerebral infarction and myocardial infarction and also to allergic inflammations such as bronchial asthma; and various thromboxane A2 antagonists, leukotriene antagonists and synthetic enzyme inhibitors have heretofore been developed. These diseases or disorders, however, actually have been shown to involve plural participating chemical mediators. Insufficient curative effects on the diseases or disorders could be obtained by a single known enzyme inhibitor or receptor antagonist.

Considering the above situation, we investigated the development of compounds and medicines having both a thromboxane A2 antagonistic effect and a leukotriene antagonistic effect.

As a result, we synthesized various phenoxyacetic acid compounds and studied their physiological activities and have found that the phenoxyacetic acid compounds of the present invention have both a thromboxane A2 antagonistic effect and a leukotriene antagonistic effect. Accordingly, we conclude that they may make up for the shortcomings of the above-mentioned single synthetic enzyme inhibitor and receptor antagonist.

The object of the present invention is to provide novel phenoxyacetic acid compounds and to provide medical preparations containing them, the novel phenoxyacetic acid compounds being antagonistic both to thromboxane A2 and leukotrienes.

SUMMARY OF THE INVENTION

The present invention, namely the above-mentioned object provides phenoxyacetic acid compounds of the following formula (I) or their physiologically acceptable salts.

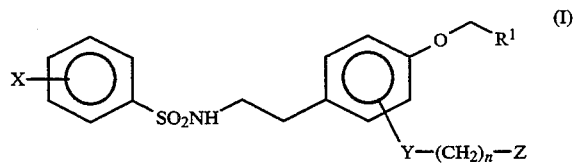

(I)

where
X is a hydrogen atom, a lower alkyl group or a halogen atom;
R1 is a carboxyl group or a lower alkoxycarbonyl group;
Y is an oxygen atom,

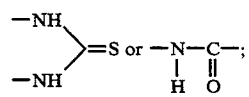

n is an integer of from 0 to 5;

Z is

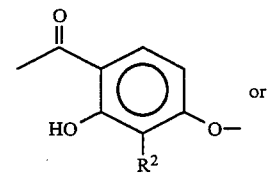

or

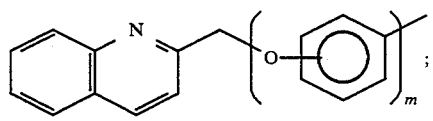

R2 is a hydrogen atom or a lower alkyl group; and m is 0 or 1.

Since the above-mentioned compounds of the present invention are a thromboxane A2 antagonist and also a leukotriene antagonist, they may be used as a medicine to prevent or cure effectively thromboxane A2- or leukotrienes-related diseases such as thrombosis or to allergic disorders such as asthma.

The thromboxane A2 antagonist mentioned above refers to a medical preparation which is a thromboxane A2 receptor and which is antagonistic to thromboxane A2; and leukotriene antagonist refers to a medical preparation which is a leukotriene receptor and which is antagonistic to leukotrienes.

The compounds of formula (I) of the present invention may also be in the form of their salts. Such salts include salts with inorganic or organic acids such as hydrochloric acid, sulfuric acid, citric acid, succinic acid or methanesulfonic acid; salts with inorganic or organic bases; alkali metal salts such as sodium salts or potassium salts; alkaline earth metal salts such as calcium salts or magnesium salts; heavy metal salts zinc salts; organic amine salts such as ammonium salts, triethylamine salts or tromethamine salts;. and amino acid salts such as arginine salts or lysine salts.

EXPLANATION OF THE PREFERRED EMBODIMENT

Formula (I) below represents the phenoxyacetic acid compounds of the present invention or their physiologically acceptable salts.

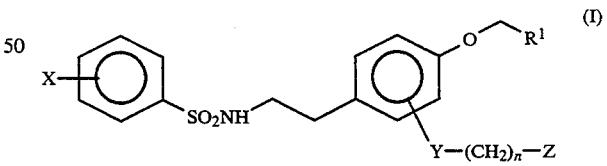

(I)

where
X is a hydrogen atom, a lower alkyl group or a halogen atom;
R1 is a carboxyl group or a lower alkoxycarbonyl group;
Y is an oxygen atom,

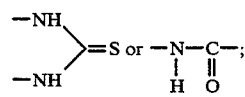

n is an integer of from 0 to 5;

Z is

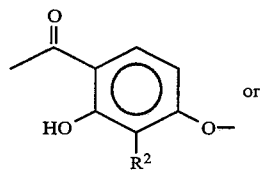

or

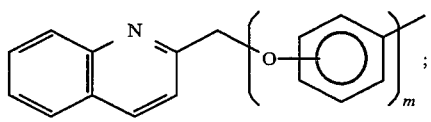

R2 is a hydrogen atom or a lower alkyl group; and m is 0 or 1.

Such phenoxyacetic acid compounds include the following compounds:

4-[2-(benzenesulfonamido)ethyl]-2-[3-(2-quinolinemethoxy)benzoylamino]phenoxyacetic acid;
4-[2-(4-chlorobenzenesulfonamido)ethyl]-2-[3-(2-quinolinemethoxy)benzoylamino]phenoxyacetic acid;
4-[2-(3-chlorobenzenesulfonamido)ethyl]-2-[3-(2-quinolinemethoxy)benzoylamino]phenoxyacetic acid,
4-[2-(2-chlorobenzenesulfonamido)ethyl]-2-[3-(2-quinolinemethoxy)benzoylamino]phenoxyacetic acid;
4-[2-(4-methylbenzenesulfonamido)ethyl]-2-[3-(2-quinolinemethoxy)benzoylamino]phenoxyacetic acid;
4-[2-4-fluorobenzenesulfonamido)ethyl]-2-[3-(2-quinolinemethoxy)benzoylamino]phenoxyacetic acid;
4-[2-(benzenesulfonamido)ethyl]-3-(2-quinolinemethoxy)phenoxyacetic acid;
4-[2-(4-chlorobenzenesulfonamido)ethyl]-3-(2-quinolinemethoxy)phenoxyacetic acid;
4-[2-(benzenesulfonamido)ethyl]-3-[3-(2-quinolinemethoxy)benzyloxy]phenoxyacetic acid;
4-[2-(4-methylbenzenesulfonamido)ethyl]-3-(2-quinolinemethoxy)phenoxyacetic acid;
4-[2-(4-chlorobenzenesulfonamido)ethyl]-3-[3-(2-quinolinemethoxy)benzyloxy]phenoxyacetic acid;
4-[2-(4-methylbenzenesulfonamido)ethyl]-3-[3-(2-quinolinemethoxy)benzyloxy]phenoxyacetic acid;
4-[2-(benzenesulfonamido)ethyl]-2-{3-[3-(2-quinolinemethoxy)phenyl]thioureido}phenoxyacetic acid;
4-[2-(4-chlorobenzenesulfonamido)ethyl]-2-{3-[3-(2-quinolinemethoxy)phenyl]thioureido}phenoxyacetic acid;
4-[2-(benzenesulfonamido)ethyl]-2-[(4-acetyl-3-hydroxy)phenoxy-4-butamido]phenoxyacetic acid;
4-[2-(4-chlorobenzenesulfonamido)ethyl]-2-[(4-acetyl-3-hydroxy)phenoxy-4-butamido]phenoxyacetic acid;
4-[2-(4-ethylbenzenesulfonamido)ethyl]-2-[(4-acetyl-3-hydroxy)phenoxy-4-butamido]phenoxyacetic acid;
4-[2-(benzenesulfonamido)ethyl]-2-[(4-acetyl-3-hydroxy-2-propyl)phenoxy-4-butamido]phenoxyacetic acid;
4-[2-(4-chlorobenzenesulfonamido)ethyl]-2-[(4-acetyl-3-hydroxy-2-propyl)phenoxy-4-butamido]phenoxyacetic acid;
4-[2-(4-methylbenzenesulfonamido)ethyl]-2-[(4-acetyl-3-hydroxy-2-propyl)phenoxy-4-butamido]phenoxyacetic acid;
4-[2-(4-fluorobenzenesulfonamido)ethyl]-2-[(4-acetyl-3-hydroxy-2-propyl)phenoxy-4-butamido]phenoxyacetic acid;
4-[2-(benzenesulfonamido)ethyl]-2-[(4-acetyl-3-hydroxy)phenoxy-5-pentamido]phenoxyacetic acid;
4-[2-(benzenesulfonamido)ethyl]-2-[(4-acetyl-3-hydroxy-2-propyl)phenoxy-5-pentamido]phenoxyacetic acid;
4-[2-(4-ethylbenzenesulfonamido)ethyl]-2-[(4-acetyl-3-hydroxy-2-propyl)phenoxy-5-pentamido]phenoxyacetic acid;
4-[2-(4-chlorobenzenesulfonamido)ethyl]-2-[(4-acetyl-3-hydroxy-2-propyl)phenoxy-5-pentamido]phenoxyacetic acid;
4-[2-(benzenesulfonamido)ethyl]-2-[(4-acetyl-3-hydroxy)phenoxy-6-hexamido]phenoxyacetic acid;
4-[2-(benzenesulfonamido)ethyl]-2-[(4-acetyl-3-hydroxy-2-propyl)phenoxy-6-hexamido]phenoxyacetic acid;
4-[2-(4-chlorobenzenesulfonamido)ethyl]-2-[(4-acetyl-3-hydroxy-2-propyl)phenoxy-6-hexamido]phenoxyacetic acid.
4-[2-(4-ethylbenzenesulfonamido)ethyl]-2-[(4-acetyl-3-hydroxy-2-propyl)phenoxy-6-hexamido]phenoxyacetic acid;
4-[2-(4-fluorobenzenesulfonamido)ethyl]-2-[(4-acetyl-3-hydroxy-2-propyl)phenoxy-6-hexamido]phenoxyacetic acid.

Phenoxyacetic acid compounds of formula (I) of the present invention are produced by the processes mentioned below.

Of the compounds of formula (I), those where Y is $$-\underset{\underset{H}{|}}{N}-\underset{\underset{O}{\parallel}}{C}-$$

and Z is

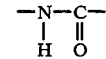

(in which R2 is a hydrogen atom or a lower alkyl group) are produced by reacting a sulfonamide derivative of a formula (II):

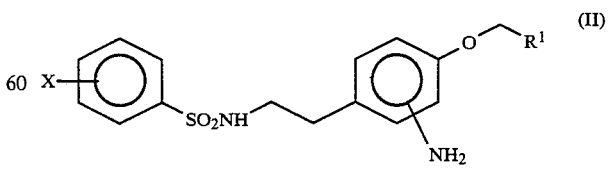

(where X is a hydrogen atom, a halogen atom or a lower alkyl group; and R1 is a carboxyl group or a lower alkoxycarbonyl group) and a carboxylic acid derivative of a formula (III):

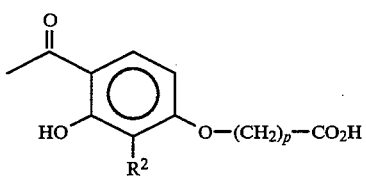

(where R2 is a hydrogen atom or a lower alkyl group; and p is an integer of from 1 to 5) with a suitable condensing agent or via a carboxylic acid active intermediate, in an inert organic solvent at a temperature of −30° C. to 100° C., but preferably −10° C. to 30° C., optionally followed by hydrolyzing the ester moiety of the resulting product.

Sulfonamide derivatives of formula (II) are obtained by subjecting a phthalimide derivative of a formula (IV):

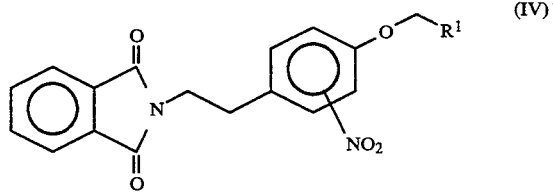

(where R1 is a carboxyl group or a lower alkyl group) to hydrazine decomposition in an inert organic solvent at −30° C. to 150° C., but preferably 50° C. to 100° C., followed by reacting the resulting amine derivative with various benzenesulfonyl chlorides in the presence of a suitable base in an inert organic solvent at −30° C. to 100° C., but preferably −10° C. to 30° C., and further followed by reduction of the nitro group in the resulting product. Carboxylic acid derivatives of formula (III) are obtained by reacting a 4-acetyl-3-hydroxy-2-alkyl-phenol and a halogenated alkanoate in the presence of a suitable base in an inert organic solvent at −30° C. to 100° C. but preferably −10° C. to 30° C., followed by the hydrolysis of the ester moiety of the resulting product.

Of the compounds of formula (I), those where Y is

and Z is

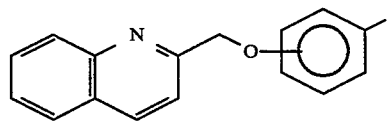

may be obtained by converting a carboxylic acid derivative of a formula (V):

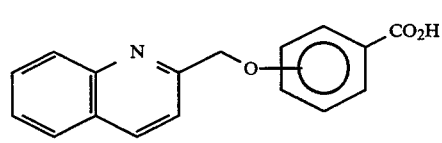

into a carboxylic acid active intermediate, followed by reacting the resulting intermediate with a sulfonamide derivative of the above formula (II) in the presence of a suitable base in an inert organic solvent at −30° C. to 100° C., but preferably −10° C. to 30° C., and optionally further followed by the hydrolysis of the ester moiety of the resulting product.

Carboxylic acid derivatives of formula (V) can be obtained by reacting 2-chloromethylquinoline and various isomeric alkyl hydroxybenzoates in the presence of a suitable base in an inert organic solvent at −30° C. to 100° C., but preferably −10° C. to 30° C., followed by the hydrolysis of the ester moiety of the resulting product.

Of the compounds of formula (I), those where Y is

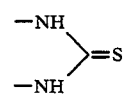

and Z is

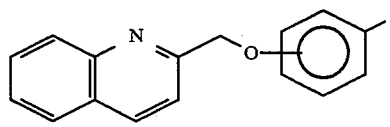

may be obtained by reacting a sulfonamide derivative of formula (II) and an isothiocyanate derivative of a formula (VI):

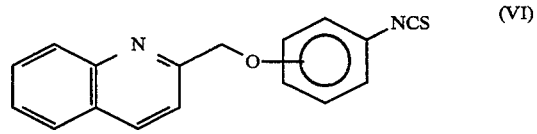

in an inert organic solvent at −30° C. to 100° C., but preferably −10° C. to 30° C., optionally followed by the hydrolysis of the ester moiety of the resulting product.

Isothiocyanate derivatives of formula (VI) can be obtained by reacting 2-chloromethylquinoline and various isomeric nitrophenols in the presence of a suitable base in an inert organic solvent at −30° C. to 100° C., but preferably −10° C. to 30° C., followed by treating the resulting product with a Raney nickel to give an amine derivative and further followed by reacting the resulting amine derivative with thiophosgene in the presence of a suitable base at −30° C. to 100° C., but preferably −10° C. to 30° C.

Of the compounds of formula (I), those where Y is an oxygen atom and Z is

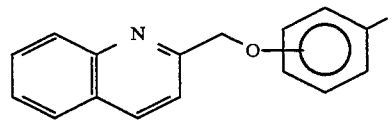

may be obtained by reacting an amine derivative of a formula (VII):

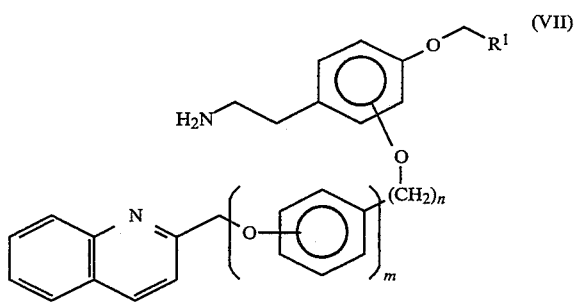

(where R1 is a carboxyl group or a lower alkyl group; n is an integer of from 0 to 5; and m is 0 or 1) with various sulfonyl chlorides in an inert organic solvent at −30° C. to 100° C. but preferably −10° C. to 30° C. optionally followed by the hydrolysis of the ester moiety of the resulting product.

Amine derivatives of formula (VII) can be obtained by reacting a phenol derivative of a formula (VIII):

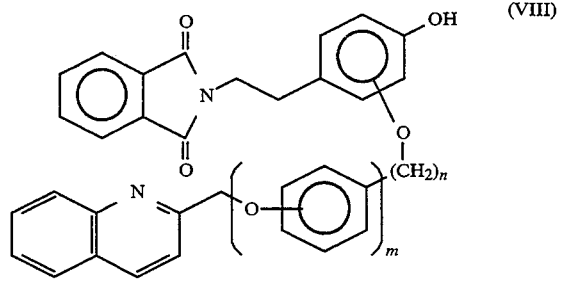

(where n is an integer of from 0 to 5; and m is 0 or 1) and an alkyl halogenoacetate in the presence of a suitable base in an inert organic solvent at −30° C. to 100° C., but preferably −10° C. to 30° C., followed by subjecting the resulting product to hydrazine decomposition.

As the condensing agent to be used in producing the compounds of the present invention can be included, for example, 1-ethyl-3-(3-dimethylaminopropyl)carbodiimide hydrochloride (WSC), dicyclohexylcarbodiimide (DCC), diphenylphosphorylazide (DPPA) and diethylpyrocarbonate (DEPC).

As examples of the base to be used to produce the compounds of the present invention, are mentioned pyridine, triethylamine, potassium carbonate, cesium carbonate and sodium hydride.

As examples of the inert organic solvent to be used to produce the compounds of the present invention, are mentioned tetrahydrofuran, aceto nitrile, ether, N,N-dimethylformamide, dimethylsulfoxide, chloroform, methylene chloride, methanol, ethanol, acetone and dioxane.

The reaction time depends upon the reaction temperature and ranges between 30 minutes and 15 hours.

The phenoxyacetic acid compounds or salts of the present invention are used medically as thromboxane A2 antagonists and leukotriene antagonists, and the dose varies depending upon the condition of the patient to which they are given. In general, the dose for an adult may be from 10 to 2000 mg/day, but preferably from 20 to 600 mg/day. Dividing the dose into one to three administrations is recommended depending on the condition of the patient. A suitable administration route may also be determined. Most preferred is peroral administration, while intravenous injection is also possible.

The compounds of the present invention may be used alone as the active ingredient or as one of the active ingredients, or they may be blended with any optional pharmaceutical carrier or excipient to be formed into various medical preparations in the form of tablets, sugar-coated pills, powders, capsules, granules, suspensions, emulsions or injections.

As examples of usable carriers and excipients, are mentioned calcium carbonate, calcium phosphate, starch, glucose, lactose, dextrin, alginic acid, mannitol, talc, and magnesium stearate.

Acute Toxicity of Compounds of formula (I):

Compounds of formula (I) were subjected to an acute toxicity test by peroral administration to ICR male mice (5 weeks of age). As a result, the $LD_{50}$ value of the compounds of the present invention was found to be 300 mg/kg or more, and the compounds were demonstrated to be highly safe in the effective amount.

EXAMPLE

Next, the present invention will be explained in more detail by way of the following examples and test example, which, however, are not intended to restrict the scope of the present invention.

EXAMPLE 1

(1) 7.58 g of potassium carbonate and 6.02 g of N-carboethoxyphthalimide were added to 180 ml of an aqueous solution of 6.01 g of 3-nitrotyramine hydrochloride and stirred for 15 hours at room temperature. 6N hydrochloric acid was gradually added to the reaction mixture at 0° C. so that the pH value of the mixture was adjusted to be 1 (one). The crystals thus precipitated out were removed by means of filtration and recrystallized from methanol to obtain 7.79 g (yield: 91%) of 4-[2-(phthalimido)ethyl]-2-nitrophenol as yellow crystals.

(2) 973 mg of potassium carbonate and 5 ml of acetone solution of 1.37 g of t-butyl bromoacetate were added to acetone (40 ml)-N,N-dimethylformamide (40 ml) solution of 2.03 g of 4-[2-(phthalimido)ethyl]-2-nitrophenol and stirred for 12 hours in an argon stream at room temperature.

The reaction mixture was diluted with ethyl acetate, poured into ice water and extracted with ethyl acetate. The organic layer was washed with a saturated saline solution and dried with anhydrous sodium sulfate. This was concentrated under reduced pressure, and the resulting residue was recrystallized from chloroform-hexane to obtain 2.46 g (yield: 90%) of t-butyl 4-[2-(phthalimido)ethyl]-2-nitrophenoxyacetate as yellow crystals.

(3) 5 ml of ethanol solution of 1.02 g of hydrazine hydrate were added to 35 ml of ethanol solution of 4.36 g of t-butyl 4-[2-(phthalimido)ethyl]-2-nitrophenoxyacetate and heated under reflux for 2 hours at 100° C. in an argon stream. After cooling, the reaction mixture was filtered through celite, and the filtrate concentrated under reduced pressure. The yellow crystals of t-butyl 4-(2-aminoethyl)-2-nitrophenoxyacetate thus obtained were used in the next reaction without purification.

1.4 ml of triethylamine were added to 15 ml of N,N-dimethylformamide solution of t-butyl 4-(2-aminoethyl)-2-nitrophenoxyacetate and stirred at 0° C. in an argon stream, and 5 ml of N,N-dimethylformamide solution of 2.37 g of p-chlorobenzenesulfonyl chloride were added thereto and stirred at room temperature for 10 hours. The reaction mixture was diluted with ethyl acetate, poured into ice water and extracted with ethyl acetate. The organic layer was washed with a saturated saline solution and dried with anhydrous sodium sulfate.

This was concentrated under reduced pressure, and the resulting residue subjected to silica gel column chromatography, whereupon 4.20 g (yield 87%) of t-butyl 4-[2-(4-chlorobenzenesulfonamido)ethyl]-2-nitrophenoxyacetate was obtained from the fraction as eluted with hexane/ethyl acetate (2/1, v/v) as a yellow oily substance.

(4) 360 mg of 10% palladium-carbon were added to 15 ml of ethyl acetate solution of 3.61 g of t-butyl 4-[2-(4-chlorobenzenesulfonamido)ethyl]-2-nitrophenoxyacetate and stirred at one atmospheric pressure in the presence of hydrogen gas. The reaction mixture was filtered and concentrated under reduced pressure. The resulting residue was subjected to silica-gel column chromatography, whereupon 2.23 g (yield 66%) of t-butyl 4-[2-(4-chlorobenzenesulfonamido)ethyl]-2-aminophenoxyacetate were obtained from the fraction as eluted with hexane/ethyl acetate (2/1, v/v) as a yellow oily substance.

(5) 2 ml of thionyl chloride were added to 874 mg of 3-(2-quinolinemethoxy)benzoic acid and stirred while cooling with ice, for 2 hours in an argon stream. The reaction mixture was concentrated under reduced pressure and dried to obtain 2-(2-quinolinemethoxy)benzoyl chloride as white crystals. This was used in the next reaction without purification.

2.2 ml of triethylamine were added to 5 ml of chloroform solution of the preceding white crystals of 3-(2-quinolinemethoxy)benzoyl chloride and stirred for 10 minutes with cooling with ice in an argon stream. To this were added 3 ml of chloroform solution of 1.38 g of t-butyl 4-[2-(4-chlorobenzenesulfonamido)ethyl]-2-aminophenoxyacetate and stirred for 11 hours at room temperature. The reaction mixture was diluted with methylene chloride, poured into ice water and extracted with methylene chloride. The organic layer was washed with a saturated saline solution and dried with anhydrous magnesium sulfate.

This was concentrated under reduced pressure, and the resulting residue was recrystallized from methylene chloride/hexane to obtain 1.83 g (yield 83%) of t-butyl 4-[2-(4-chlorobenzenesulfonamido)ethyl]-2-[3-(2-quinolinemethoxy)benzoylamino]phenoxyacetate as white crystals.

(6) 1.0 ml of trifluoroacetic acid was added to 5 ml of methylene chloride solution of 360 mg of t-butyl 4-[2-(4-chlorobenzenesulfonamido)ethyl-2-[3-(2-quinolinemethoxy)benzoylamino]phenoxyacetate while cooling with ice and stirred at room temperature for 16 hours in an argon stream.

The reaction mixture was concentrated under reduced pressure, and the resulting residue was recrystallized from tetrahydrofuran/hexane to obtain 110 mg (yield 61%) of 4-[2-(4-chlorobenzenesulfonamido)ethyl]-2-[3-(2-quinolinemethoxy)benzoylamino]phenoxyacetic acid as white crystals.

The spectroscopic data of the product support the structure of the following formula (IX):

NMR (CDCl$_3$—CD$_3$OD) δ: 2.72 (2H, t, J=7 Hz), 2.93-3.74 (2H, m), 4.68 (2H, s), 5.53 (2H, s), 6.80-8.44 (17H, m)

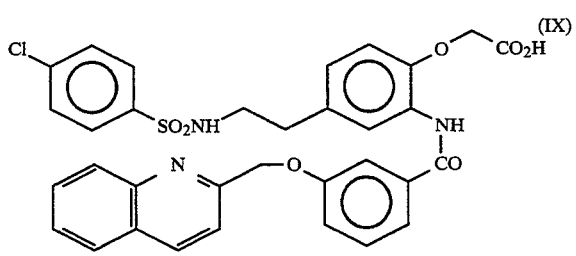

EXAMPLE 2

Using t-butyl 4-( 2-aminoethyl )-2-nitrophenoxyacetate and benzenesulfonyl chloride in an argon stream, obtained was 4-[2-(benzenesulfonylamino)ethyl ]-2-[3-(2-quinolinemethoxy)benzoylamino]phenoxyacetic acid in accordance with the same process as in Example 1. The spectroscopic data of the product support the structure of the following formula (X):

NMR (CDCl$_3$—CD$_3$OD) δ: 2.37-2.90 (2H, m), 3.20 (2H, t, J=8 Hz), 4.69 (2H, s), 5.52 (2H, s), 6.81-8.44 (18H, m)

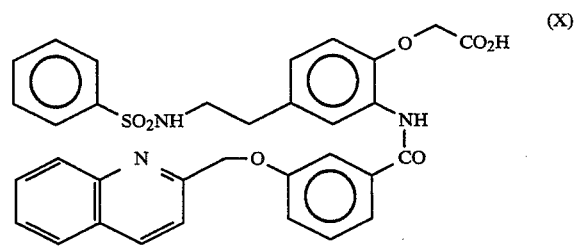

EXAMPLE 3

(1) One ml of ethanol solution of hydrazine hydrate was added to 2 ml of ethanol solution of 340 mg of ethyl 4-[2-(phthalimido)ethyl]-3-(2-quinolinemethoxy)-phenoxyacetate at room temperature and heated under reflux at 100° C. for 2 hours, in an argon stream. The precipitates thus crystallized out were removed by means of filtration and concentrated under reduced pressure until dry.

73 μl of triethylamine were added to 2 ml of N,N-dimethylformamide solution of the residue obtained above, while cooling with ice and stirred for 10 minutes in an argon stream, and 111 mg of p-chlorobenzenesulfonyl chloride were added thereto. After stirring for 16 hours at room temperature, ice water was added to the reaction mixture, which was then extracted with ethyl acetate. The organic layer was washed with a saturated saline solution and dried with anhydrous sodium sulfate.

This was concentrated under reduced pressure, and the resulting residue was subjected to silica gel column chromatography, whereupon 130 mg (35%) of ethyl 4-[2-(4-chlorobenzenesulfonamido)ethyl]-3-(2-quinolinemethoxy)phenoxyacetate was obtained from the fraction as eluted with hexane/ethyl acetate (1/1, v/v) as a yellow oily substance.

(2) 0.2 ml of 2N sodium hydroxide aqueous solution were added to 2 ml of tetrahydrofuran solution of 130 mg of ethyl 4-[2-(4-chlorobenzenesulfonamido)ethyl]-3-(2-quinolinemethoxy)phenoxyacetate and stirred at room temperature for 4 hours in an argon stream. The solvent was removed by distillation under reduced pressure, and the pH value of the residue was adjusted to be 1 (one) by adding diluted hydrochloric acid.

The crystals thus precipitated out were removed by means of filtration and dried under reduced pressure, and these were subjected to silica gel column chromatography, whereupon 80 mg (yield 66%) of 4-[2-(4-chlorobenzenesulfonamido)ethyl]-3-(2-quinolinemethoxy)phenoxyacetic acid were obtained as white crystals from the fraction as eluted with 10% methanol/chloroform.

The spectroscopic data of the product support the structure of the following formula (XI):

NMR (CDCl$_3$—CD$_3$OD) δ: 2.70 (2H, m), 3.18 (2 H, m), 4.30 (2H, m), 5.00 (2H, s), 6.23–8.10 (13H, m)

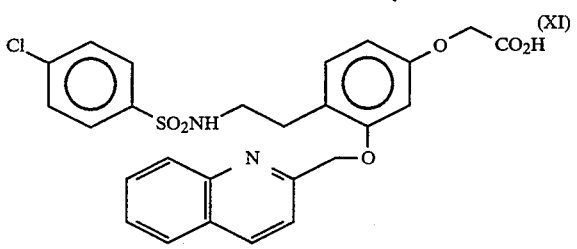

(XI)

EXAMPLE 4

Using ethyl 4-[2-(phthalimido)ethyl ]-3-[3-(2-quinolinemethoxy)benzyloxy]phenoxyacetate and hydrazine hydrate in an argon stream, ethyl 4-[2-(4-chlorobenzenesulfonamido)ethyl ]-3-[3-(2-quinolinemethoxy)benzyloxy]phenoxyacetate was obtained in accordance with the same process as in Example 3. The spectroscopic data of the product support the structure of the following formula (XII):

NMR (CDCl$_3$) δ: 1.31 (3H, t, J=7 Hz), 2.70 (2H, m), 3.20 (2H, m), 4.28 (2H, q, J=7 Hz), 4.53 (2H, s), 4.90 (2H, s), 5.40 (2H, s), 5.45 (1H, brs), 6.20–8.2.3 (17H, m)

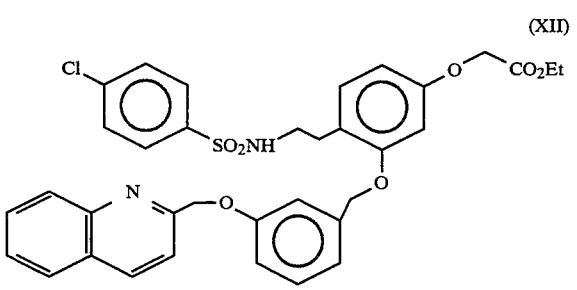

(XII)

Next, 0.05 ml of 2N sodium hydroxide aqueous solution was added to one ml of tetrahydrofuran solution of 48 mg of ethyl 4-[2-(4-chlorobenzenesulfonamido)ethyl]-3-[3-(2-quinolinemethoxy)benzyloxy]phenoxyacetate (formula XII) and stirred for 12 hours at room temperature in an argon stream. The solvent was then removed by distillation under reduced pressure, and the pH value of the residue was adjusted to be 1 (one) by adding diluted hydrochloric acid.

The crystals thus precipitated out were removed by means of filtration and dried under reduced pressure; these were, then, subjected to silica gel column chromatography whereupon 32 mg (yield 69%) of 4-[2-(4-chlorobenzenesulfonamido)ethyl]-3-(3-(2-quinolinemethoxy)benzyloxy]phenoxyacetic acid were obtained as white crystals from the fraction eluted with 10% methanol/chloroform.

The spectroscopic data of the product support the structure of the following formula (XIII):

NMR (CDCl$_3$+CD$_3$OD) δ: 2.70 (2H, m), 3.20 (2H, m) 4.53 (2H, S), 4.88 (2H, S), 5.40 (2H, S), 6.20–8.23 (17H, m)

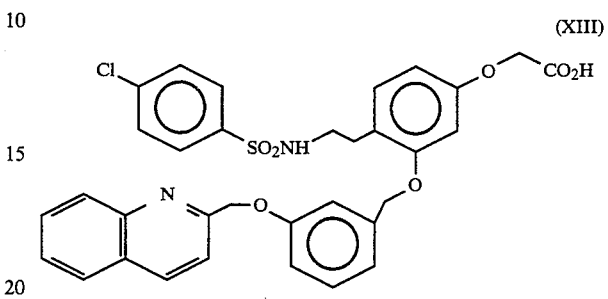

(XIII)

EXAMPLE 5

(1) 5 ml of methylene chloride solution of 860 ml of 3-(2-quinolinemethoxy)aminophenol and 5 ml of aqueous solution of 728 mg of anhydrous sodium carbonate were simultaneously dropwise added to 0.26 ml of thiophosgene and stirred for one hour at room temperature. Water was added to the reaction mixture, which was then extracted with chloroform and dried with anhydrous magnesium sulfate. This was concentrated under reduced pressure, and the resulting residue was subjected to silica gel column chromatography whereupon 890 mg (yield 94%) of 3-(2-quinolinemethoxy)-phenylisothiocyanate were obtained as white crystals from the fraction as eluted with hexane/ethyl acetate (2/1, v/v).

(2) 356 mg of 3-(2-quinolinemethoxy)phenyl isothiocyanate were added to 3 ml of chloroform solution of 570 mg of t-butyl 4-[2-(4-chlorobenzenesulfonamido)ethyl]-2-aminophenoxyacetate and stirred for 12 hours at room temperature in an argon stream. Ice water was added to the reaction mixture, which was then extracted with methylene chloride. The organic layer was washed with a saturated saline solution and dried with anhydrous magnesium sulfate.

This was concentrated under reduced pressure, and the resulting residue subjected to silica gel column chromatography whereupon 740 mg (yield 80%) of t-butyl 4-[2-(4-chlorobenzenesulfonamido)ethyl]-2-{3-[3-(2-quinolinemethoxyphenyl]thioureido}phenoxyacetate were obtained as a pale yellow oily substance from the fraction as eluted with hexane/ethyl acetate (2/1, v/v).

This was, then, processed in the same manner as in Example 1, and 600 mg (yield 78% ) of 4-[2-(4-chlorobenzenesulfonamido)ethyl ]-2-{3-[3-(2-quinolinemethoxy)phenyl]thioureido}phenoxyacetic acid were obtained as pale yellow crystals.

The spectroscopic data of the product support the structure of the following formula (XIV):

NMR (CDCl$_3$—CD$_3$OD) δ: 2.35–2.70 (2H, m), 2.80–3.20 (2H, m), 4.39 (2H, brs), 5.20 (2H, brs), 6.10–9.25 (17H, m)

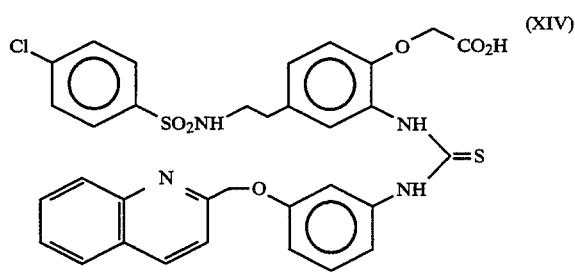

(XIV)

EXAMPLE 6

(1) 631 mg of 1-ethyl-3-(3-dimethylaminopropyl)carbodiimide hydrochloride (WSC) were added to 5 ml of methylene chloride solution of 839 mg of 4-(4-acetyl-3-hydroxy-2-propylphenoxy)butyric acid and stirred for 10 minutes while cooling with ice in an argon stream, and 3 ml of methylene chloride solution of 1.32 g of t-butyl 4-[2-(4-chlorobenzenesulfonamido)ethyl]-2-aminophenoxyacetate were added thereto and stirred for 12 hours at room temperature. The reaction mixture was diluted with methylene chloride, poured into ice water and extracted with methylene chloride. The organic layer was washed with a saturated saline solution and dried with anhydrous magnesium sulfate. This was concentrated under reduced pressure, and the resulting residue was subjected to silica-gel column chromatography whereupon 1.30 g (yield 62%) of t-butyl 4-[2-(4-chlorobenzenesulfonamido)ethyl]-2-[(4-acetyl-3-hydroxy-2-propyl)phenoxy-4-butamido]phenoxyacetate were obtained as white crystals from the fraction as eluted with hexane/ethyl acetate (2/1, v/v ).

(2 ) 0.5 ml of trifluoroacetic acid were added to 3 ml of methylene chloride solution of 440 mg of t-butyl 4-[2-(4-chlorobenzenesulfonamido)ethyl]-2-[(4-acetyl-3-hydroxy-2-propyl )phenoxy-4-butamido]phenoxyacetate while cooling with ice and stirred for 10 hours at room temperature in an argon stream. The reaction mixture was concentrated under reduced pressure, and the resulting residue was recrystallized from chloroform/hexane to obtain 290 mg (yield 71%) of 4-[2-(4-chlorobenzenesulfonamido)ethyl]-2-[(4-acetyl-3-hydroxy-2-propyl)phenoxy-4-butamido]phenoxyacetic acid as white crystals. The spectroscopic data of the product support the structure of the following formula (XV):

NMR (CDCl₃—CD₃OD) δ: 0.86 (3H, t, J=8 Hz), 1.17-1.76 (2H, ), 1.89-2.83 (8H, m), 2.50 (3 H, s), 2.89-3.26 (2H, m), 4.07 (2H. t, J=6 Hz), 5.26 (2H, brs), 6.20-8.89 (9H, m)

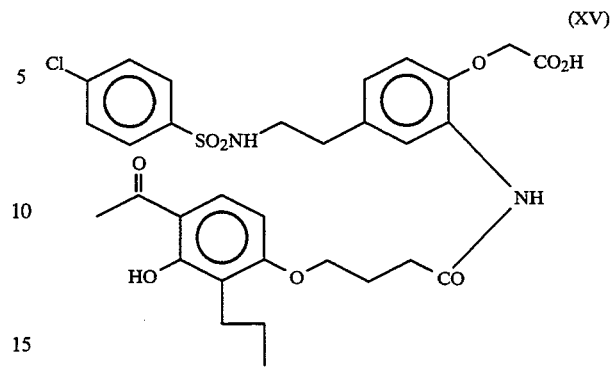

(XV)

EXAMPLE 7

Using 5-(4-acetyl-3-hydroxy-2-propylphenoxy)valeric acid and t-butyl 4-[2-(4-chlorobenzenesulfonamido)ethyl]-2-aminophenoxyacetate, white crystals of 4-[2-(4-chlorobenzenesulfonamido)ethyl]-2-[(4-acetyl-3-hydroxy-2-propyl)phenoxy-5-pentamido]phenoxyacetic acid were obtained in accordance with the same process as in Example 6. The spectroscopic data of the product support the structure of the following formula (XVI):

NMR (CDCl₃-CD₃OD) δ: 0.87 (3H, t, J=7 Hz), 1.15-2.12 (6H, m), 2.36-2.87 (6H, m) 2.51 (3 H, s), 3.15 (2H, t, J=6 Hz), 3.90-4.21 (2H, m), 4.57 (2H, brs), 6.33-8.03 (9H, m)

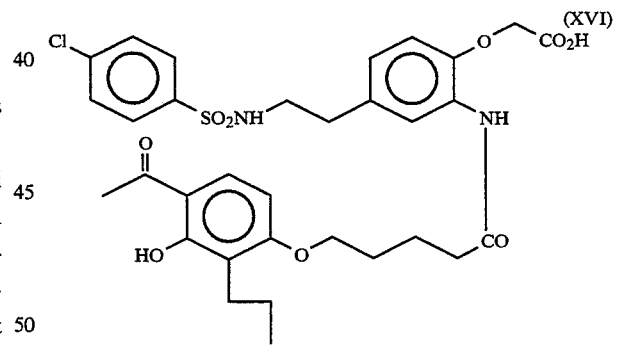

(XVI)

EXAMPLE 8

Using 6-(4-acetyl-3-hydroxy-2-propylphenoxy)caproic acid and t-butyl 4-[2-(4-chlorobenzenesulfonamido)ethyl]phenoxyacetate, white crystals of 4-[2-(4-chlorobenzenesulfonamido)ethyl]-2-[(4-acetyl-3-hydroxy-2-propyl)phenoxy-6-hexamido]phenoxyacetic acid were obtained in accordance with the same process as in Example 6. The spectroscopic data of the product support the structure of the following formula (XVII):

NMR (DMSO—d₆) δ: 0.82 (3H, t, J=6 Hz), 1.17-3.13 (16H, m), 2.51 (3H, s), 3.93-4.40 (5H, m), 6.47-8.16 (10H, m), 10.84 (1H, brs), 12.80 (1H, brs)

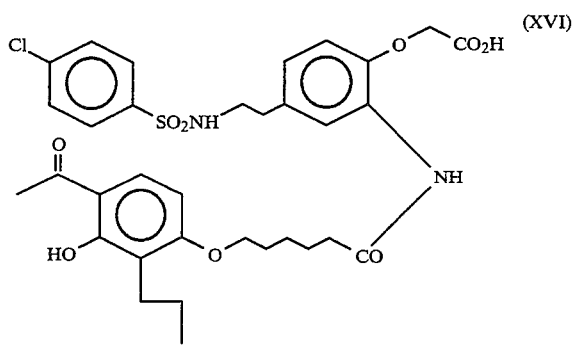

(XVI)

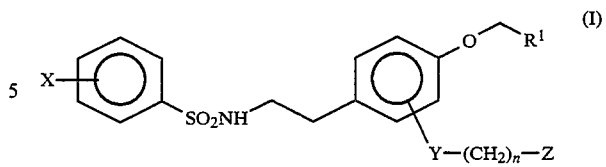

(I)

where
X is a hydrogen atom, a lower alkyl group or a halogen atom;

R1 is a carboxyl group or a lower alkoxycarbonyl group;

Y is an oxygen atom,

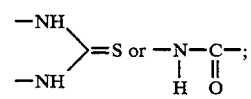

n is an integer of from 0 to 5;
Z is

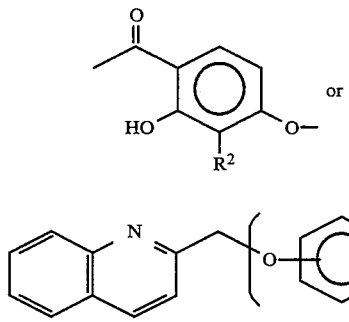

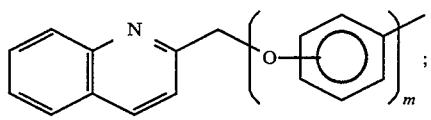

R2 is a hydrogen atom or a lower alkyl group; and m is 0 or 1.

2. A composition containing the phenoxyacetic acid compounds of formula (I) according to claim 1 or their physiologically acceptable salts.

3. A method for treating a disease or disorder treatable by administration of a thromboxane A2 antagonist comprising administering an effective amount of a compound according to claim 1 or a physiologically acceptable salt thereof.

4. The method of claim 3 wherein the disease or disorder is an ischemic disease.

5. A method for treating a disease or condition associated with thromboxane A2 and/or leukotrienes and treatable by the administration of a thromboxane A2 antagonist and/or comprising a leukotriene antagonist administering an effective amount of a compound according to claim 1 or a physiologically acceptable salt thereof.

6. A method for treating a disease or condition associated with leukotrienes and treatable by the administration of a leukotriene antagonist comprising administering an effective amount of a leukotriene antagonist compound according to claim 1 or a physiologically acceptable salt thereof.

7. A method for treating an allergic condition comprising administering an effective amount of a compound according to claim 1 or a physiologically acceptable salt thereof.

8. The method of claim 7 wherein said allergic condition is an inflammatory condition.

TEST EXAMPLE

The compounds of the present invention displayed an antagonistic effect as shown in Table 1 below to thromboxane A2 (TXA2) and leukotriene D4 (LTD4) in the in vitro system mentioned below. The in vitro $IC_{50}$ value of the antagonistic effect of the compounds of the present invention to TXA2 and LTD4 was obtained, using the following test system. Tracheal strips isolated from Hartley male guinea pigs (weight: 300 to 500 g) were suspended under a tension of 0.3 g in a Tyrode solution at 37° C. in an organ bath, to which a mixed gas of oxygen (95%)-carbon dioxide (5%) was introduced. After letting the above stabilize for about one hour, TXA2 (produced by Cayman Co.) or LTD4 (produced by Wako Pure Chemicals CO.) was added to the organ bath in a concentration-of $10^{-7}M$ and $10^{-8}M$ respectively, whereupon the contraction of the sections was measured as a standard. The strips were treated with various amounts of the compounds of Examples 1–8, whereupon the contraction of the tracheal preparations upon dosing with TXA2 or LTDS4 was again measured. From the values thus measured, the $IC_{50}$ (Inhibition concentration) of the compound added was calculated. The results are shown in Table 1 below; the smaller the amount of the compound, the stronger its effectiveness.

TABLE 1

| Example No. | Antagonistic Effect ($IC_{50}$) | |
| --- | --- | --- |
| | TXA2 | LTD4 |
| 1 | $4.2 \times 10^{-9}M$ | $6.5 \times 10^{-8}M$ |
| 2 | $3.4 \times 10^{-9}M$ | $3.8 \times 10^{-8}M$ |
| 3 | $3.5 \times 10^{-9}M$ | $8.3 \times 10^{-6}M$ |
| 4 | $5.9 \times 10^{-7}M$ | $2.1 \times 10^{-7}M$ |
| 5 | $2.5 \times 10^{-8}M$ | $7.2 \times 10^{-8}M$ |
| 6 | $8.2 \times 10^{-9}M$ | $1.6 \times 10^{-7}M$ |
| 7 | $1.9 \times 10^{-8}M$ | $7.6 \times 10^{-8}M$ |
| 8 | $4.0 \times 10^{-8}M$ | $2.6 \times 10^{-7}M$ |

As is noted from the results in Table 1 above, the compounds of the present invention displayed an excellent antagonistic effect to TXA2 and LTD4. Though not shown in Table 1, also the other compounds of the present invention (not only those illustrated) displayed an excellent antagonistic effect to TXA2 and LTD4.

What is claimed is:

1. Phenoxyacetic acid compounds of the following formula (I) or their physiologically acceptable salts:

9. The method of claim 8 wherein said inflammatory condition is bronchial asthma.

10. The method of claim 3 wherein said thromboxane A2 related disease or condition is an ischemic disease.

11. The method of claim 10 wherein said disease is selected from the group consisting of cerebral infarction and myocardial infarction.

12. The method of claim 6 wherein said leukotriene related disease or condition is an ischemic disease.

13. The method of claim 12 wherein said disease is selected from the group consisting of cerebral infarction and myocardial infarction.

14. A pharmaceutical composition suitable for treatment of a leukotriene and/or a thromboxane A2 related condition or disease which comprises an effective amount of at least one compound according to claim 1 and a pharmaceutically acceptable carrier.

15. The pharmaceutical composition of claim 14 wherein said leukotriene and/or thromboxane A2 related condition or disease is selected from the group consisting of cerebral infarction, myocardial infarction and allergic conditions.

16. The phenoxyacetic acid compound of claim 1 wherein said compound is selected from the following compounds:

4-[2-(benzenesulfonamido)ethyl]-2-[3-(2-quinolinemethoxy)benzoylamino]phenoxyacetic acid;

4-[2-(4-chlorobenzenesulfonamido)ethyl]-2-[3-(2-quinolinemethoxy)benzoylamino]phenoxyacetic acid;

4-[2-(3-chlorobenzenesulfonamido)ethyl]-2-[3-(2-quinolinemethoxy)benzoylamino]phenoxyacetic acid;

4-[2-(2-chlorobenzenesulfonamido)ethyl]-2-[3-(2-quinolinemethoxy)benzoylamino]phenoxyacetic acid;

4-[2-(4-methylbenzenesulfonamido)ethyl]-2-[3-(2-quinolinemethoxy)benzoylamino]phenoxyacetic acid;

4-[2-4-fluorobenzenesulfonamido)ethyl]-2-[3-(2-quinolinemethoxy)benzoylamino]phenoxyacetic acid;

4-[2-(benzenesulfonamido)ethyl]-3-(2-quinolinemethoxy)phenoxyacetic acid;

4-[2-(4-chlorobenzenesulfonamido)ethyl]-3-(2-quinolinemethoxy)phenoxyacetic acid;

4-[2-(benzenesulfonamido)ethyl]-3-[3-(2-quinolinemethoxy)benzyloxy]phenoxyacetic acid;

4-[2-(4-methylbenzenesulfonamido)ethyl]-3-(2-quinolinemethoxy)phenoxyacetic acid;

4-[2-(4-chlorobenzenesulfonamido)ethyl]-3-[3-(2-quinolinemethoxy)benzyloxy]phenoxyacetic acid;

4-[2-(4-methylbenzenesulfonamido)ethyl]-3(3-(2-quinolinemethoxy)benzyloxy]phenoxyacetic acid;

4-[2-(benzenesulfonamido)ethyl]-2-{3-[3-(2-quinolinemethoxy)phenyl]thioureido}phenoxyacetic acid;

4-[2-(4-chlorobenzenesulfonamido)ethyl]-2-{3-[3-(2-quinolinemethoxy)phenyl]thioureido}phenoxyacetic acid;

4-[2-(benzenesulfonamido)ethyl]-2-[(4-acetyl-3-hydroxy)phenoxy-4-butamido]phenoxyacetic acid;

4-[2-(4-chlorobenzenesulfonamido)ethyl]-2-[(4-acetyl-3-hydroxy)phenoxy-4-butamido]phenoxyacetic acid;

4-[2-(4-ethylbenzenesulfonamido)ethyl]-2-[(4-acetyl-3-hydroxy)phenoxy-4-butamido]phenoxyacetic acid;

4-[2-(benzenesulfonamido)ethyl]-2-[(4-acetyl-3-hydroxy-2-propyl)phenoxy-4-butamido]phenoxyacetic acid;

4-[2-(4-chlorobenzenesulfonamido)ethyl]-2-[(4-acetyl-3-hydroxy-2-propyl)phenoxy-4-butamido]phenoxyacetic acid;

4-[2-(4-methylbenzenesulfonamido)ethyl]-2-[(4-acetyl-3-hydroxy-2-propyl)phenoxy-4-butamido]phenoxyacetic acid;

4-[2-(4-fluorobenzenesulfonamido)ethyl]-2-[(4-acetyl-3-hydroxy-2-propyl)phenoxy-4-butamido]phenoxyacetic acid;

4-[2-(benzenesulfonamido)ethyl]-2-[(4-acetyl-3-hydroxy)phenoxy-5-pentamido]phenoxyacetic acid;

4-[2-(benzenesulfonamido)ethyl]-2-[(4-acetyl-3-hydroxy-2-propyl)phenoxy-5-pentamido]phenoxyacetic acid;

4-[2-(4-ethylbenzenesulfonamido)ethyl]-2-[(4-acetyl-3-hydroxy-2-propyl)phenoxy-5-pentamido]phenoxyacetic acid;

4-(2-(4-chlorobenzenesulfonamido)ethyl]-2-[(4-acetyl-3-hydroxy-2-propyl)phenoxy-5-pentamido]phenoxyacetic acid;

4-[2-(benzenesulfonamido)ethyl]-2-[(4-acetyl-3-hydroxy)phenoxy-6-hexamido]phenoxyacetic acid;

4-[2-(benzenesulfonamido)ethyl]-2-[(4-acetyl-3-hydroxy-2-propyl)phenoxy-6-hexamido]phenoxyacetic acid;

4-[2-(4-chlorobenzenesulfonamido)ethyl]-2-[(4-acetyl-3-hydroxy-2-propyl)phenoxy-6-hexamido]phenoxyacetic acid;

4-[2-(4-ethylbenzenesulfonamido)ethyl]-2-[(4-acetyl-3-hydroxy-2-propyl)phenoxy-6-hexamido]phenoxyacetic acid;

4-[2-(4-fluorobenzenesulfonamido)ethyl]-2-[(4-acetyl-3-hydroxy-2-propyl)phenoxy-6-hexamido]phenoxyacetic acid.

17. A pharmaceutical composition suitable for treatment of a thromboxane A2 and/or a leukotriene related disease or condition which contains at least one phenoxyacetic compound according to claim 16 and a pharmaceutically acceptable carrier.

18. The method of claim 6 wherein the leukotriene is LTD4.

* * * * *

UNITED STATES PATENT AND TRADEMARK OFFICE
CERTIFICATE OF CORRECTION

PATENT NO. : 5,360,909
DATED : November 1, 1994
INVENTOR(S) : Azuma IGARASHI et al It is certified that error appears in the above-indentified patent and that said Letters Patent is hereby corrected as shown below:

In Column 10, line 3, delete "Cl" and insert -- $C\ell$ --.

In Column 11, line 17, delete "Cl" and insert -- $C\ell$ --.

In Column 11, line 39, delete "8.2.3" and insert -- 8.23 --.

In Column 11, line 44, delete "Cl" and insert -- $C\ell$ --.

In Column 12, line 12, delete "Cl" and insert -- $C\ell$ --.

In Column 12, line 66, delete "($CDCl_3$-" and insert -- ($CDCL_3$- --.

In Column 13, line 4, delete "Cl" and insert -- $C\ell$ --.

In Column 13, line 64, delete "($CDCl_3$-" and insert -- ($CDCL_3$- --.

In Column 13, line 65, delete "(2H, )" and insert -- (2H, m) --.

In Column 13, line 66, delete "(2H. t, " and insert -- (2H, t, --.

In Column 14, line 4, delete "Cl" and insert -- $C\ell$ --.

In Column 14, line 31, delete "($CDCl_3$-" and insert -- ($CDCL_3$- --.

In Column 15, line 4, delete "Cl" and insert -- $C\ell$ --.

Signed and Sealed this

First Day of August, 1995

Attest:

BRUCE LEHMAN

Attesting Officer

Commissioner of Patents and Trademarks